United States Patent
Marine Do Nascimento et al.

(10) Patent No.: US 11,662,347 B2
(45) Date of Patent: May 30, 2023

(54) METHOD FOR THE DIAGNOSIS OF SYSTEMIC LUPUS ERYTHEMATOSUS (SLE)

(71) Applicants: UNIVERSITAT POLITECNICA DE VALENCIA, Valencia (ES); INSTITUTO DE INVESTIGACION SANITARIA LA FE—FUNDACION PARA LA INVESTIGACION DEL HOSPITAL UNIVERSITA, Valencia (ES); UNIVERSITAT DE VALENCIA ESTUDI GENERAL, Valencia (ES)

(72) Inventors: Noelle Marine Do Nascimento, Valencia (ES); David Gimenez Romero, Valencia (ES); Sergi Benat Morais Ezquerro, Valencia (ES); Angel Maquieira Catala, Valencia (ES); Augusto Miguel Juste Dolz, Valencia (ES); Elena Grau Garcia, Valencia (ES); Rosa Puchades Pla, Valencia (ES); Jose Andres Roman Iborra, Valencia (ES)

(73) Assignees: UNIVERSITAT POLITECNICA DE VALENCIA, Valencia (ES); INSTITUTO DE INVESTIGACION SANITARIA LA FE—FUNDACION PARA LA INVESTIGACION DEL HOSPITAL UNIVERSITARIO Y POLITECNICO LA FE DE LA COMUNIDAD VALENCIANA, Valencia (ES); UNIVERSITAT DE VALENCIA ESTUDI GENERAL, Valencia (ES)

( * ) Notice: Subject to any disclaimer, the term of this patent is extended or adjusted under 35 U.S.C. 154(b) by 310 days.

(21) Appl. No.: 16/634,266

(22) PCT Filed: Jun. 29, 2018

(86) PCT No.: PCT/ES2018/070467
§ 371 (c)(1),
(2) Date: Jan. 27, 2020

(87) PCT Pub. No.: WO2019/020847
PCT Pub. Date: Jan. 31, 2019

(65) Prior Publication Data
US 2021/0364513 A1 Nov. 25, 2021

(30) Foreign Application Priority Data

Jul. 26, 2017 (ES) .................... ES201730972

(51) Int. Cl.
G01N 33/53 (2006.01)
G01N 33/564 (2006.01)
G01N 33/543 (2006.01)

(52) U.S. Cl.
CPC ..... *G01N 33/564* (2013.01); *G01N 33/54373* (2013.01); *G01N 2800/24* (2013.01)

(58) Field of Classification Search
None
See application file for complete search history.

(56) References Cited

U.S. PATENT DOCUMENTS 5,501,986 A 3/1996 Ward et al.

FOREIGN PATENT DOCUMENTS

| GB | WO2014124280 A1 * | 8/2014 | ........... G01N 33/487 |
|---|---|---|---|
| WO | 9635103 A1 | 11/1996 | |
| WO | 2008114003 A1 | 9/2008 | |

OTHER PUBLICATIONS

Carbone et al., Potential role of serum BAFF as a biomarker in HIV infection, Infectious Diseases, 2015; 47, pp. 260-262. (Year: 2015).*
Pohanka, The piezoelectric biosensors: principles and applications, a review, Int. J. Electrochem. Sci., 12, 2017 pp. 496-506, published Dec. 12, 2016. (Year: 2016).*
Noelle M. Do Nascimento, et al., "Label-Free Piezoelectric Biosensor for Prognosis and Diagnosis of Systemic Lupus Erythematosus", Biosensors and Bioelectronics, vol. 90, pp. 166-173, 2016.
Noelle M. Do Nascimento, et al., "The Ro/SSA Complex in Systemic Lupus Erythematosus Patients. Thesis Doctoral", Universitat Politecnica de Valencia. Department of Chemistry, 3 pages, Feb. 2017.
Matthew C. Dixon, "Quartz Crystal Microbalance With Dissipation Monitoring: Enabling . . . ", Journal of Biomolecular Techniques, vol. 19, No. 3, pp. 151-158, 2008.
International Search Report and Written Opinion for International Application No. PCT/ES2018/070467 (10 Pages) (Nov. 8, 2018).

* cited by examiner

*Primary Examiner* — Gary Counts
(74) *Attorney, Agent, or Firm* — Lucas & Mercanti, LLP

(57) ABSTRACT

A method for the diagnosis of systemic lupus erythematosus (SLE) based on an interfacial process of antigen-antibody molecular recognition, specifically between anti-Ro52 and Ro52 protein, in a piezoelectric resonator, for application in the diagnosis of autoimmune diseases such as SLE.

1 Claim, 1 Drawing Sheet

METHOD FOR THE DIAGNOSIS OF SYSTEMIC LUPUS ERYTHEMATOSUS (SLE)

CROSS REFERENCE TO RELATED APPLICATION

This Application is a 371 of PCT/ES2018/070467 filed on Jun. 29, 2018, which claims the benefit of Spanish Patent Application No. P201730972, filed Jul. 26, 2017, which is incorporated herein by reference.

FIELD OF THE INVENTION

The present invention relates to the technical field of the diagnosis of autoimmune diseases, and specifically to following an interfacial process of antigen-antibody molecular recognition in a piezoelectric resonator, as well as the screening of samples from autoimmune patients.

BACKGROUND OF THE INVENTION

Anti-Ro/SSA antibodies are antinuclear antibodies (ANA) which are associated with many autoimmune diseases, such as systemic lupus erythematosus (SLE), Sjögren's syndrome (SS), SS/SLE overlap syndrome, sub-acute cutaneous lupus erythematosus (SOLE) and neonatal lupus. They constitute an auxiliary immunological study in the diagnosis of patients with autoimmune diseases such as lupus erythematosus (LE), or as predictors for the prognosis of some vasculitis of Sjögren's syndrome (SS). Anti-Ro antibodies were described for the first time 30 years ago in a patient with SLE with polyserositis, photosensitivity and negative for antinuclear antibodies (ANA).

SLE is the non-organ-specific autoimmune disease par excellence, since the body produces a number of antibodies (Ab) targeting its own cellular structures, which ultimately results in inflammatory lesions of multiple organs and systems. SLE is the disease that is most associated with the Ro antigen (anti-Ro).

The Ro antigen is a ribonucleoprotein made up of RNA and a protein portion which is especially located in the cell cytoplasm (hence the name scRNP, small cytoplasmic ribonucleoproteins). In the protein portion there are at least four different antigen polypeptides with sizes ranging between 52 (Ro52) and 60 kD (Ro60), capable of reacting with an anti-Ro monospecific serum.

With regard to the quantitative methods for diagnosis, several assays have been developed for the determination of autoantibodies, including ELISA, immunoblot immunoassays, multiple flow immunoassay and protein arrays. The key advantages of these assays are that they are easy to use, flexible and low-cost. However, the main limitation refers to the low sensitivity, which limits the determination of extremely low concentrations of circulating serum antibodies. Therefore, the development of highly sensitive biosensors is of enormous interest for determining autoantibodies at very low concentrations.

The quartz crystal microbalance (QCM) technique has been used extensively as a biosensor because it works well, is highly sensitive and presents low limits of detection, offering excellent advantages over conventional detection techniques. In particular, quartz crystal microbalances with dissipation (QCM-D) present significant advantages in relation to sensitivity. Furthermore, QCM-D is appealing due to the response of the sensor in the form of variations in the dissipation factor ($\Delta D$) which is related to viscoelasticity, which in turn is associated with structural changes in the film adhered to the QCM-D transducer. This adds complementary information in relation to structural interactions between probe and target, showing a high potential for diagnosing and predicting autoimmune diseases such as SLE. These biosensors operate under the principle that a change in mass resulting from the interaction between the antibody and its respective antigen can be determined directly.

U.S. Pat. No. 5,501,986A describes a method for detecting an analyte (proteins, hormones, enzymes, antibodies, carbohydrates or nucleic acids) in a sample using QCM, measuring the change in resonance frequency and correlating the change in frequency with the amount of analyte in the sample. However, the method only relates the presence of an analyte with a single variable.

Common measurements in piezoelectric experiments correspond to surface concentration and reaction time measurements, without taking into account the viscoelastic properties of the adhered layer. As a result, transition states cannot be detected by this conventional measurement methodology during surface processes because the monitored signal cannot be separated out. To solve this problem, the simultaneous measurement of resonance frequency (f) (adhered mass) and the dissipation factor (D) (viscoelastic properties) were introduced in the new piezoelectric sensors. Interfacial processes can thereby be analyzed as a function of the nature of the surface thereof. The major problem with this approach is that it does not directly introduce the measurement time, therefore it cannot be measured in situ and the temporal analysis of the monitored process is furthermore made more complex.

One example is patent WO2008114003A1, which describes a method and apparatus for detecting the presence and/or amount of an oligomer analyte (antibody) in a sample by means of a piezoelectric biosensor, wherein ratios between different variables such as resonance frequency and the dissipation factor are established. This invention relates to the detection of certain diseases, in particular Alzheimer's.

Use of a function ($-df/dD$) which allows introducing the time factor in the structural study of the interface monitored by QCM-D has recently been published in Biosensors & Bioelectronics 2017, 90, 166. However, this function has two clear limitations: its interpretation implies highly skilled personnel, and it is not very sensitive, so it has little discrimination capacity.

DESCRIPTION OF THE INVENTION

The present invention solves the problems existing in the state of the art by means of a method for the diagnosis of autoimmune diseases in a human. Said method is based on the measurement in a piezoelectric resonator of the ratio between different variables, such as surface concentration and the quality factor, by means of the function $d\Delta\Gamma/d\Delta Q$ of an interfacial process of antigen-antibody molecular recognition for screening samples from autoimmune patients.

Function $d\Delta\Gamma/d\Delta Q$ monitors structural changes involved in the deposition of a reactive species on the surface of a piezoelectric crystal. Certain approaches are needed for the clear interpretation of its meaning:

The acoustic response of a piezoelectric sensor (of density "$\rho_0$", thickness "$h_0$" and elastic shear modulus "$\mu_0$") coated with a viscoelastic film (of density "$\rho_1$", thickness "$h_1$", shear viscosity "$\eta_1$" and elastic shear modulus "$\mu_1$")

immersed in a Newtonian fluid (of shear viscosity "$\eta_3$" and viscous penetration depth "$\delta_3$") is modeled by means of the following expressions:

$$\Delta\Gamma \approx \frac{A\sqrt{\rho_0 \mu_0}}{2f^2} \frac{1}{2\pi\rho_0 h_0}\left[\frac{\eta_3}{\delta_3} + h_1\rho_1 w - 2h_1\left(\frac{\eta_3}{\delta_3}\right)^2 \frac{\eta_1 w^2}{\mu_1^2 + w^2 \eta_1^2}\right] \quad (1)$$

$$\Delta Q \approx -\frac{D_0}{2\pi f \rho_0 h_0 Q_0}\left[\frac{\eta_3}{\delta_3} + 2h_1\left(\frac{\eta_3}{\delta_3}\right)^2 \frac{\mu_1 w}{\mu_1^2 + w^2 \eta_1^2}\right] \quad (2)$$

wherein "Q" is the quality factor, "D" is the dissipation factor and "f" is the resonance frequency of the piezoelectric sensor (FIG. 1).

When considering a pure elastic film ($\eta_1 \to 0$) and accordingly:

$$\Delta\Gamma \approx \frac{A\sqrt{\rho_0 \mu_0}}{2f^2} \frac{1}{2\pi\rho_0 h_0}\left[\frac{\eta_3}{\delta_3} + h_1\rho_1 w\right] \quad (3)$$

$$\Delta Q \approx -\frac{D_0}{2\pi f \rho_0 h_0 Q_0}\left[\frac{\eta_3}{\delta_3} + 2h_1\left(\frac{\eta_3}{\delta_3}\right)^2 \frac{w}{\mu_1}\right] \quad (4)$$

by deriving both expressions as a function of monitoring time (t), the following is obtained:

$$\frac{d\Delta\Gamma}{dt} \approx \frac{A\sqrt{\rho_0 \mu_0}}{2f^2} \frac{1}{2\pi\rho_0 h_0} \frac{d(h_1\rho_1 w)}{dt} \overset{w\to cte}{\approx} \frac{A\sqrt{\rho_0 \mu_0}}{2f^2} \frac{w}{2\pi\rho_0 h_0} \frac{d(h_1\rho_1)}{dt} \quad (5)$$

$$\frac{d\Delta Q}{dt} \approx -\frac{D_0}{2\pi f \rho_0 h_0 Q_0} 2\left(\frac{\eta_3}{\delta_3}\right)^2 \frac{d}{dt}\left(\frac{h_1 w}{\mu_1}\right) \overset{w\to cte}{\approx}$$

$$-\frac{wD_0}{2\pi f \rho_0 h_0 Q_0} 2\left(\frac{\eta_3}{\delta_3}\right)^2 \frac{d}{dt}\left(\frac{h_1}{\mu_1}\right). \quad (6)$$

and by dividing them (($\partial\Delta\Gamma/\partial t$)/($\partial\Delta Q/\partial t$)), function $\partial\Delta\Gamma/\partial\Delta Q$ (8) is obtained:

$$\frac{d\Delta\Gamma}{d\Delta Q} = \frac{\frac{d\Delta\Gamma}{dt}}{\frac{d\Delta Q}{dt}} \approx -\frac{A\sqrt{\rho_0 \mu_0}}{2f} \frac{Q_0 \delta_3^2}{D_0 2\eta_3^2} \frac{\frac{d(h_1\rho_1)}{dt}}{\frac{d}{dt}\left(\frac{h_1}{\mu_1}\right)} = \quad (7)$$

$$-\frac{A\sqrt{\rho_0 \mu_0}}{2f} \frac{Q_0 \delta_3^2}{D_0 2\eta_3^2} \frac{d(h_1\rho_1)}{d\left(\frac{h_1}{\mu_1}\right)} == -\frac{A\sqrt{\rho_0 \mu_0}}{2f} \frac{Q_0 \delta_3^2}{D_0 2\eta_3^2}$$

$$\left(h_1 \frac{d(\rho_1)}{d\left(\frac{h_1}{\mu_1}\right)} + \rho_1 \frac{d(h_1)}{d\left(\frac{h_1}{\mu_1}\right)}\right) \overset{h_1\to cte}{\approx} -\frac{A\sqrt{\rho_0 \mu_0}}{2f} \frac{Q_0 \delta_3^2}{D_0 2\eta_3^2} \frac{d\rho_1}{d\left(\frac{1}{\mu_1}\right)}$$

$$\frac{d\Delta\Gamma}{d\Delta Q} \approx -\frac{A\sqrt{\rho_0 \mu_0}}{2f} \frac{Q_0 \delta_3^2}{D_0 2\eta_3^2} \frac{d\rho_1}{d\left(\frac{1}{\mu_1}\right)} \quad (8)$$

Equation (8) shows how function $d\Delta\Gamma/d\Delta Q$ is directly proportional to the variation of the density of the film adhered to the sensor surface with respect to the inverse of its viscoelastic properties. Therefore, if the film adhered to a piezoelectric surface is modified only by one process, the value of the function $\partial\Delta\Gamma/\partial\Delta Q$ will remain constant over the transformation time, given that function:

$$d\rho_1 \Big/ d\left(\frac{1}{\mu_1}\right)$$

will be constant.

In that case, each adhered species will regularly modify the viscoelastic properties of the film monitored by the piezoelectric sensor. However, if the monitored transformation corresponds to multiple parallel or consecutive processes, the function $d\Delta\Gamma/d\Delta Q$ will vary over time presenting n−1 maximums, wherein n corresponds to the number of species constituted during the transformation process. Therefore, said function allows unequivocally characterizing the transformation processes of the films adhered on piezoelectric materials by both their evolution over time and by the time values they have.

Therefore, a first aspect of the invention is a method for the diagnosis of autoimmune diseases in a human comprising two steps:

(a) incubating a sample obtained from said human in a piezoelectric resonator comprising a protein antigen immobilized on the surface of the resonator and determining the value of the function $d\Delta\Gamma/d\Delta Q$ described in function (8), and (b) performing the diagnosis of autoimmune diseases by determining the maximum value of $d\Delta\Gamma/d\Delta Q$, where the diagnosis is positive when the maximum is greater than a cutoff value of 600 ng/cm$^2$.

In another aspect of the invention, the autoimmune diseases for which this method is suitable include Sjögren's syndrome (SS), systemic lupus erythematosus (SLE) and neonatal lupus erythematosus (NLE).

In another aspect of the invention, the protein antigen used for the diagnosis of the aforementioned diseases is the Ro protein antigen (anti-Ro). Specifically, the protein antigen is Ro52 since the conformational changes implied by molecular recognition are very different between patients and healthy subjects.

Systemic lupus erythematosus (SLE) is the disease which is most associated with anti-Ro, with a reported average positivity of 27.7%, which increases up to 45 to 50% when analyzed by ELISA. In the case of a late onset LE (over 50 years old), positivity is 92%.

Furthermore, anti-Ro is an important disease marker in neonatal lupus erythematosus (NLE), since over 90% of mothers and their babies express it, although the prevalence of NLE in anti-Ro mothers is 1%. Anti-Ro is also present in 70 to 88% of patients with primary Sjögren's syndrome (SS) and in 10 to 50% of secondary cases.

In another aspect of the invention, the sample incubated in step (a) of the method is obtained from the blood serum of the patient for whom the diagnosis of the aforementioned autoimmune diseases is to be performed.

DESCRIPTION OF EMBODIMENTS

Example 1. Study of the Interaction Antibody Anti-Ro52/Ro52 Protein

The chemical immobilization of specific autoantigens in the piezoelectric resonator and the determination of circulating autoantibodies were performed.

Ro52 protein was immobilized by covalent anchoring, forming a self-assembled monolayer. The monolayer was created by submerging the piezoelectric surface for 16 h in a 10 mM mercaptopropionic acid solution and subsequent activation by 10 mM EDC/NHS for 60 min. Next, the surface was treated with 5 mM carbohydrazide for 60 min. Then 100 μL of Ro52 protein (33 mg/L) were dispensed on the sensor surface, being incubated for 60 min. Finally, the free active residues were blocked by means of treating the sensor surface with an aqueous solution containing EDTA, BSA and Polysorbate (TWEEN 20) at 0.05%, pH 8.5.

The antibodies were purified from the serum of anti-Ro+ patients.

Next, the variation of the surface concentration and the quality factor during the selective interaction of autoantigens with specific autoantibodies present in a PBS1x solution was recorded using a piezoelectric sensor.

Subsequently, function $\partial\Delta\Gamma/\partial\Delta Q$, wherein "Γ" is the surface concentration and "Q" is the quality factor, during the studied molecular recognition process was calculated (FIG. 2a). FIG. 2a shows the fingerprint characteristic of the molecular recognition process, presenting a maximum value at 3,000 ng/cm² at 1,000 seconds. Therefore, as described above, this function shows that the monitored process corresponds to cooperative binding. The antibodies bind the antigen by means of a specific epitope-paratope interaction, for the Fc fragment of these antibodies to subsequently be recognized by the PRY-SPRY domain of Ro52 protein. This experiment demonstrates the use of the function to monitor transition states and molecular recognition patterns, establishing reaction pathways of the studied process.

Figure 1:
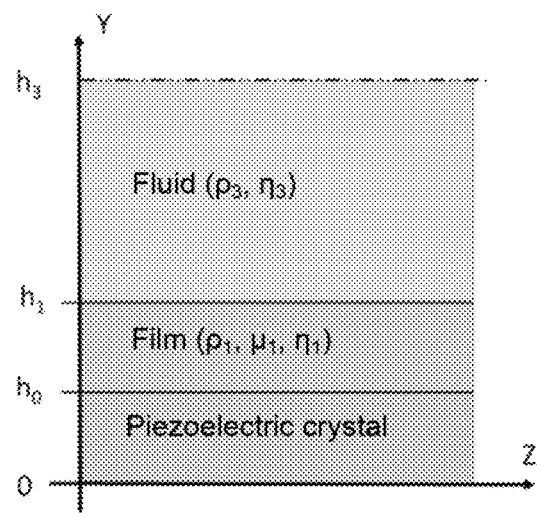
FIG. 1. Representation of the geometry of a piezoelectric crystal coated with a viscoelastic film (general depiction of a concept that is known in the state of the art).
Figure 2:
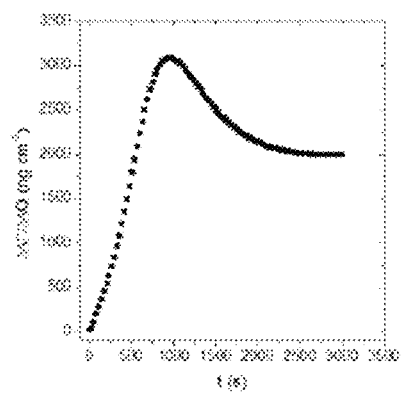
FIG. 2. Graphic representation of function $d\Delta\Gamma/d\Delta Q$ over time during the interaction of Ro52 protein with autoantibodies coming from anti-Ro+ autoimmune patients (a) and healthy individuals (b).
Figure 2:
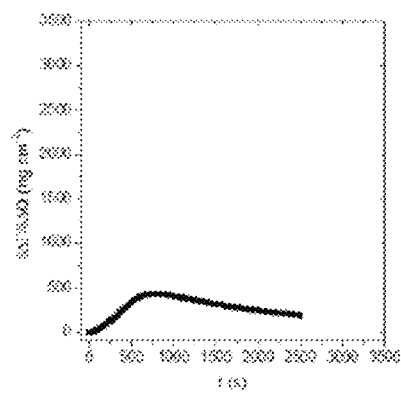

Example 2. Study of the Application of Function dΔΓ/dΔQ in Healthy Patients and Anti-Ro+ Autoimmune Patients To demonstrate the goodness of use of function dΔΓ/dΔQ for the discrimination of patients with autoimmune diseases, the molecular recognition of anti-Ro52 antibodies from anti-Ro+ autoimmune patients and healthy individuals was studied. As shown in FIG. 2, the antibodies of both populations show a similar recognition behavior when represented over time.

The pattern shown is a function with a peak shape having a maximum value around 1,000 seconds. Therefore, both processes have one and the same cooperative reaction mechanism. However, the antibodies from anti-Ro+ patients have a maximum value close to 3,000 ng/cm².

This characteristic pattern remains unchanged when solutions containing anti-Ro52 antibodies of a population of 130 anti-Ro+ autoimmune patients are analyzed. In contrast, when the serum of healthy patients is analyzed, the antibody recognition pattern presents a maximum value at 500 ng/cm².

Therefore, function $\partial\Delta\Gamma/\partial\Gamma Q$ allows unequivocally discriminating anti-Ro+ patients by establishing a cutoff value at 600 ng/cm², identifying characteristic recognition patterns.

The invention claimed is:

1. A method for real time quantification of circulating autoantibodies in a human suffering from systemic lupus erythematosus (SLE), comprising:
   (a) incubating a blood serum sample obtained from said human in a piezoelectric resonator, wherein the piezoelectric resonator comprises a protein antigen Ro52 immobilized on a surface of the resonator forming a self-assembled monolayer and dispensing Ro52 protein on the surface such that a selective interaction of autoantigens with specific autoantibodies are obtained;
   (b) measuring, in the piezoelectric resonator, a variation of a surface concentration dΔΓ and a variation of a quality factor dΔQ during the selective interaction of autoantigens with specific autoantibodies;
   (c) determining a maximum value of dΔΓ/dΔQ with respect to time through formula $$\frac{d\Delta\Gamma}{d\Delta Q} \approx -\frac{A\sqrt{\rho_0\mu_0}}{2f}\frac{Q_0\delta_3^2}{D_0 2\eta_3^2}d\left(\frac{1}{\mu_1}\right)$$

wherein
   ΔΓ is a surface concentration shift and ΔQ is a quality factor shift,
   A is a surface area of the resonator,
   $\rho_0$ is a density, $D_0$ is a dissipation factor, $\mu_0$ is an elastic shear modulus, and $Q_0$ is a quality factor of the piezoelectric sensor,
   f is a resonance frequency,
   $\rho_1$ is a density and $\mu_1$ is an elastic shear modulus of a viscoelastic film coating the sensor, and
   $\eta_3$ is a shear viscosity and $\delta_3$ is a viscous penetration depth of a Newtonian fluid in which a film is immersed,
   wherein the maximum value of dΔΓ/dΔQ is greater than 600 ng/cm².

* * * * *